(12) United States Patent
Thakur et al.

(10) Patent No.: US 10,799,187 B2
(45) Date of Patent: Oct. 13, 2020

(54) SYSTEMS AND METHODS TO DETECT RESPIRATORY DISEASES

(71) Applicant: Cardiac Pacemakers, Inc., St. Paul, MN (US)

(72) Inventors: Pramodsingh Hirasingh Thakur, Woodbury, MN (US); Jeffrey E. Stahmann, Ramsey, MN (US); Michael J. Kane, Roseville, MN (US); Bin Mi, Plymouth, MN (US); Ron A. Balczewski, Bloomington, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 655 days.

(21) Appl. No.: 15/604,039

(22) Filed: May 24, 2017

(65) Prior Publication Data
US 2017/0347969 A1    Dec. 7, 2017

Related U.S. Application Data

(60) Provisional application No. 62/344,067, filed on Jun. 1, 2016.

(51) Int. Cl.
*A61B 5/00*    (2006.01)
*A61B 7/00*    (2006.01)
(Continued)

(52) U.S. Cl.
CPC .......... *A61B 5/7282* (2013.01); *A61B 5/0205* (2013.01); *A61B 5/029* (2013.01);
(Continued)

(58) Field of Classification Search
CPC .......... A61B 5/00; A61B 5/02; A61B 5/0205; A61B 5/029; A61B 5/0295; A61B 7/00;
(Continued)

(56) References Cited

U.S. PATENT DOCUMENTS

| 6,949,075 B2 | 9/2005 | Hatlesad et al. |
| 7,678,058 B2 * | 3/2010 | Patangay ............. A61B 5/0205 600/484 |

(Continued)

FOREIGN PATENT DOCUMENTS

WO    WO-2017210055 A1    12/2017

OTHER PUBLICATIONS

Jardin, Francois, et al., "Mechanism of Paradoxic Pulse in Bronchial Asthma", Circulation, 66, No. 4, [Online]. Retrieved from the Internet: <URL: http://circ.ahajournals.org/, (Oct. 1982), 887-894.

(Continued)

*Primary Examiner* — Eric J Messersmith
(74) *Attorney, Agent, or Firm* — Schwegman Lundberg & Woessner, P.A.

(57) ABSTRACT

Systems and methods for monitoring patients with respiratory diseases are described. A system may include a sensor circuit to sense a respiration signal and at least one hemodynamic signal. The system may detect a specified respiratory phase from the respiration signal, and generate from the hemodynamic signal one or more signal metrics that are correlative to at least one of a systolic blood pressure, a blood volume, or a cardiac dimension. The system may detect a restrictive or obstructive respiratory condition when the hemodynamic signal metric indicates hemodynamic deterioration during a specified respiratory phase. The system may additionally classify the detected restrictive or
(Continued)

obstructive respiratory condition into one of two or more categories, and deliver a therapy based on the detection or the classification.

20 Claims, 5 Drawing Sheets

(51) Int. Cl.
| | |
|---|---|
| *A61B 5/02* | (2006.01) |
| *A61N 1/365* | (2006.01) |
| *A61B 5/08* | (2006.01) |
| *A61N 1/36* | (2006.01) |
| *A61B 5/0205* | (2006.01) |
| *A61B 5/029* | (2006.01) |
| *A61B 5/0295* | (2006.01) |
| *A61B 7/02* | (2006.01) |
| *A61B 7/04* | (2006.01) |
| *A61B 5/11* | (2006.01) |
| *A61B 5/021* | (2006.01) |
| *A61B 5/024* | (2006.01) |
| *A61B 5/0245* | (2006.01) |
| *A61B 5/053* | (2006.01) |
| *A61B 5/085* | (2006.01) |

(52) U.S. Cl.
CPC ........ *A61B 5/02028* (2013.01); *A61B 5/0295* (2013.01); *A61B 5/08* (2013.01); *A61B 5/4809* (2013.01); *A61B 5/4818* (2013.01); *A61B 5/4836* (2013.01); *A61B 5/6801* (2013.01); *A61B 5/6846* (2013.01); *A61B 5/6867* (2013.01); *A61B 5/7246* (2013.01); *A61B 5/7264* (2013.01); *A61B 7/003* (2013.01); *A61B 7/023* (2013.01); *A61B 7/04* (2013.01); *A61N 1/3601* (2013.01); *A61N 1/3611* (2013.01); *A61N 1/36514* (2013.01); *A61B 5/021* (2013.01); *A61B 5/0245* (2013.01); *A61B 5/02416* (2013.01); *A61B 5/053* (2013.01); *A61B 5/085* (2013.01); *A61B 5/0816* (2013.01); *A61B 5/0826* (2013.01); *A61B 5/1116* (2013.01); *A61B 5/1118* (2013.01); *A61B 5/4561* (2013.01)

(58) Field of Classification Search
CPC ........... A61B 7/02; A61B 7/04; A61B 5/7282; A61B 7/003; A61B 5/6801; A61B 5/6867; A61B 5/02028; A61B 5/4863; A61B 5/6846; A61B 5/7264; A61B 5/7246; A61B 7/023; A61B 5/08; A61B 5/4809; A61B 5/4818; A61B 5/1118; A61B 5/1116; A61B 5/021; A61B 5/0826; A61B 5/0245; A61B 5/02416; A61B 5/053; A61B 5/4561; A61B 5/0816; A61B 5/085; A61N 1/36514; A61N 1/3601; A61N 1/3611
See application file for complete search history.

(56) References Cited

U.S. PATENT DOCUMENTS

| | | | |
|---|---|---|---|
| 7,853,327 B2 | 12/2010 | Patangay et al. | |
| 8,096,954 B2 | 1/2012 | Stahmann et al. | |
| 2006/0020295 A1* | 1/2006 | Brockway | A61N 1/36521 607/17 |
| 2006/0077063 A1 | 4/2006 | Cheng et al. | |
| 2008/0071185 A1* | 3/2008 | Beck | A61B 5/0816 600/529 |
| 2008/0119749 A1 | 5/2008 | Haro et al. | |
| 2011/0105858 A1 | 5/2011 | Cho | |
| 2013/0137997 A1* | 5/2013 | Patangay | A61B 7/00 600/483 |
| 2015/0282738 A1* | 10/2015 | Thakur | A61B 5/7275 600/528 |

OTHER PUBLICATIONS

Pasterkamp, Hans, et al., "Respiratory Sounds—Advances Beyond the Stethoscope", Am I Respir Crit Care Med, vol. 156, (1997), 974-987.

"International Application Serial No. PCT/US2017/034212, International Preliminary Report on Patentability mailed Dec. 13, 2018", 7 pgs.

"International Application Serial No. PCT/US2017/034212, International Search Report dated Sep. 27, 2017", 4 pgs.

"International Application Serial No. PCT/US2017/034212, Written Opinion dated Sep. 27, 2017", 7 pgs.

* cited by examiner

SYSTEMS AND METHODS TO DETECT RESPIRATORY DISEASES

CLAIM OF PRIORITY

This application claims the benefit of priority under 35 U.S.C. § 119(e) of U.S. Provisional Patent Application Ser. No. 62/344,067, filed on Jun. 1, 2016, which is herein incorporated by reference in its entirety.

TECHNICAL FIELD

This document relates generally to medical devices, and more particularly, to systems and methods for monitoring patients with a respiratory disease.

BACKGROUND

Asthma and chronic obstructive pulmonary disease (COPD) are common chronic respiratory conditions that may affect a large population. Although asthma affects people of all ages, children and adolescents are disproportionately affected by the disease compared to other age groups. Asthma is caused by inflammation and tightening of the airway muscles, which narrows the airways. COPD is a progressive respiratory disease that may be characterized by decreased airflow over time, as well as inflammation of the tissues that line the airway. COPD include two main conditions, namely emphysema and chronic bronchitis. COPD is one of the major comorbidities in patients with chronic diseases such as congestive heart failure (CHF), which is a leading cause of death in the United States.

Asthma and COPD may coexist in some patients. About 40% of COPD patients also have asthma. In addition, asthma is considered a clinical risk factor for developing COPD. Both asthma and COPD, among some other respiratory diseases, may have similar symptoms, which may include chronic coughing, wheezing, shortness of breath, or hyper-responsiveness to airflow during inspiration, among others. Compared to patients with COPD, lung function is only fully reversible in patients with asthma.

Ambulatory medical devices may be used to monitor patients with chronic disease. Some ambulatory medical devices include physiological sensors that may sense physiological signals from the patient. The ambulatory medical devices may deliver therapy such as electrical stimulations to target tissues or organs. For example, implantable cardiac devices may deliver electrical therapies to restore or improve the cardiac function. Some of these devices may provide diagnostic features.

Respiratory diseases such as asthma and COPD may have a huge economic impact on the healthcare system. Proper monitoring of patient with respiratory diseases such as asthma or COPD may improve the accuracy and reliability in detecting restrictive or obstructive respiratory conditions prior to needing an inhaler or to administer appropriate therapies to prevent worsening of respiratory conditions, thereby reducing healthcare cost associated with the treatment and hospitalization.

SUMMARY

This document discusses, among other things, a patient management system for monitoring patients with respiratory diseases. The system may include a sensor circuit to sense a respiration signal and at least one hemodynamic signal. During a specified respiratory phase detected from the respiration signal, the system may generate from the hemodynamic signal one or more hemodynamic parameters that are correlative to at least one of a systolic blood pressure, a blood volume, or a cardiac dimension. The system may detect a restrictive or obstructive respiratory condition when the hemodynamic signal metric indicates hemodynamic deterioration during a specified respiratory phase such as during inspiration. The system may additionally classify the detected restrictive or obstructive respiratory condition into one of two or more categories, and deliver a therapy based on the detection or the classification.

Example 1 is a system for managing a respiratory disease in a patient. The system comprises a sensor circuit including sense amplifier circuits to sense one or more physiological signals including a respiration signal and at least one hemodynamic signal, a signal processor circuit configured to detect from the respiration signal a respiratory phase within a respiratory cycle and generate from the sensed at least one hemodynamic signal, during the detected respiratory phase, one or more hemodynamic parameters correlative to at least one of a systolic blood pressure, a blood volume, or a cardiac dimension, and a detector circuit coupled to the signal processor circuit and configured to detect a target restrictive or obstructive respiratory condition in response to the one or more hemodynamic parameters satisfying a specified condition during the detected respiratory phase.

In Example 2, the subject matter of Example 1 optionally includes an output circuit configured to provide the detected restrictive or obstructive respiratory condition to a user or a process.

In Example 3, the subject matter of any one or more of Examples 1-2 optionally includes the detector circuit that may be configured to detect the target restrictive or obstructive respiratory condition in response to the one or more hemodynamic parameters indicates hemodynamic deterioration during at least a portion of an inspiration phase.

In Example 4, the subject matter of any one or more of Examples 1-3 optionally includes the sensor circuit coupled to a wearable or implantable accelerometer sensor or a microphone sensor to sense the respiration signal.

In Example 5, the subject matter of any one or more of Examples 1-4 optionally includes the sensor circuit coupled to a heart sound sensor to sense the at least one hemodynamic signal including a heart sound signal. The signal processor circuit may generate the one or more hemodynamic parameters including one or more of first (S1), second (S2), third (S3) and fourth (S4) heart sounds from the sensed heart sound signal during an inspiration or respiration phase of the respiration signal.

In Example 6, the subject matter of Example 5 optionally includes the detector circuit that may be configured to detect the restrictive or obstructive respiratory condition in response to: a S1 heart sound intensity during an inspiration phase exceeding a first threshold; or a rate of change of the S1 heart sound intensity during an inspiration phase exceeding a second threshold.

In Example 7, the subject matter of any one or more of Examples 5-6 optionally includes the detector circuit that may be configured to detect the restrictive or obstructive respiratory condition in response to: a S2 heart sound intensity during an inspiration phase falling below a first threshold; or a rate of change of the S2 heart sound intensity during an inspiration phase exceeding a second threshold.

In Example 8, the subject matter of any one or more of Examples 5-7 optionally includes the detector circuit that may be configured to detect the restrictive or obstructive respiratory condition in response to an intensity of the S1 heart sound during an inspiration phase relative to an intensity of the S1 heart sound during an expiration phase exceeding a threshold.

In Example 9, the subject matter of any one or more of Examples 5-8 optionally includes the signal processor circuit that may be configured to generate the one or more hemodynamic parameters including a relative intensity between one of the S1, S2, S3, or S4 heart sound and another of the S1, S2, S3, or S4 heart sound.

In Example 10, the subject matter of any one or more of Examples 5-9 optionally includes the signal processor circuit that may be configured to generate the one or more hemodynamic parameters including a cardiac timing interval using the S1, S2, S3, or S4 heart sound.

In Example 11, the subject matter of any one or more of Examples 1-10 optionally includes the signal processor circuit that may be configured to generate from the at least one hemodynamic signal the one or more hemodynamic parameters including: a heart rate; a cardiac or thoracic pressure metric; a left ventricular (LV) or right ventricular (RV) systolic volume, diastolic volume, or stroke volume metric; an ejection time; a cardiac output metric; a ratio of early to late ventricular filling velocities; a cardiac or thoracic impedance metric; or a photo plethysmography metric.

In Example 12, the subject matter of any one or more of Examples 1-11 optionally includes a physiological sensor configured to sense a signal indicative of respiratory sounds, wherein the detector circuit is configured to detect the restrictive or obstructive respiratory condition further using the respiratory sounds.

In Example 13, the subject matter of any one or more of Examples 1-12 optionally includes a classifier circuit configured to: trend the one or more hemodynamic parameters; and classify the detected restrictive or obstructive respiratory condition into one of two or more categories of restrictive or obstructive respiratory diseases using the trended one or more hemodynamic parameters. The two or more categories of the restrictive or obstructive respiratory diseases may include wheezing, asthma, bronchoconstriction, chronic obstructive pulmonary disease, bronchiectasis, acute bronchitis, pulmonary fibrosis, pneumoconiosis, acute respiratory distress syndrome, or sleep apnea.

In Example 14, the subject matter of Example 13 optionally includes one or more of: a physical activity detector to detect a physical activity intensity; a posture detector to detect a posture of the patient; or a sleep detector to detect a sleep or awake state, wherein the classifier circuit is to classify the detected restrictive or obstructive respiratory condition further using one or more of the detected physical activity level, the patient posture, or the sleep or awake state.

In Example 15, the subject matter of any one or more of Examples 13-14 optionally includes the classifier circuit that may be configured to discriminate an asthma from an obstructive sleep apnea using at least the trended one or more hemodynamic parameters.

Example 16 is a method for detecting a respiratory condition in a patient using a respiratory disease management system. The method comprises steps of: sensing, via an implantable or wearable physiological sensor, one or more physiological signals including a respiration signal and at least one hemodynamic signal; detecting from the respiration signal a respiratory phase within a respiratory cycle; generating one or more hemodynamic parameters using the sensed at least one hemodynamic signal during the detected respiratory phase, the one or more hemodynamic parameters correlative to at least one of a systolic blood pressure, a blood volume, or a cardiac dimension; detecting a target restrictive or obstructive respiratory condition in response to the one or more hemodynamic parameters satisfying a specified condition during the detected respiratory phase; and providing the detected restrictive or obstructive respiratory condition to a user or a process.

In Example 13, the subject matter of Example 16 optionally includes generating a signal to trigger or adjust a therapy delivered to the patient.

In Example 18, the subject matter of any one or more of Examples 16-17 optionally includes the step of detecting the target restrictive or obstructive respiratory condition that may include detecting a hemodynamic deterioration from the one or more hemodynamic parameters during at least a portion of an inspiration phase.

In Example 19, the subject matter of any one or more of Examples 16-18 optionally includes the at least one hemodynamic signal which may include a heart sound signal and the one or more hemodynamic parameters include one or more of a first (S1), second (S2), third (S3) and fourth (S4) heart sounds from the sensed heart sound signal.

In Example 20, the subject matter of Example 19 optionally includes the step of detecting the restrictive or obstructive respiratory condition which may include determining an intensity, or a rate of change of intensity, of one or more of S1, S2, S3, or S4 heart sounds during an inspiration phase satisfying a specified condition.

In Example 21, the subject matter of any one or more of Examples 19-20 optionally includes the one or more hemodynamic parameters that may include: a relative intensity between one of the S1, S2, S3, or S4 heart sound and another of the S1, S2, S3, or S4 heart sound; or a cardiac timing interval using the S1, S2, S3, or S4 heart sound.

In Example 22, the subject matter of any one or more of Examples 16-21 optionally includes sensing a signal indicative of respiratory sounds, wherein detecting the restrictive or obstructive respiratory condition further includes using the respiratory sounds.

In Example 23, the subject matter of any one or more of Examples 16-22 optionally includes steps of trending the one or more hemodynamic parameters and classifying the detected restrictive or obstructive respiratory condition into one of two or more categories of restrictive or obstructive respiratory diseases using the trended one or more hemodynamic parameters. The two or more categories of the restrictive or obstructive respiratory diseases may include wheezing, asthma, bronchoconstriction, chronic obstructive pulmonary disease, bronchiectasis, acute bronchitis, pulmonary fibrosis, pneumoconiosis, acute respiratory distress syndrome, or sleep apnea.

The systems, devices, and methods discussed in this document may improve the medical technology of automated monitoring of patients with respiratory disease. The detection of a restrictive or obstructive respiratory condition based on systolic blood pressure during a respiratory phase may enhance the performance and functionality of a medical system or an ambulatory medical device for detecting a respiratory disease. In certain examples, the enhanced device functionality may include more timely detection of respiratory anomaly with increased accuracy at little to no additional cost. The improvement in system performance and functionality, provided by the present systems and methods, can reduce healthcare costs associated with management and hospitalization of patients with respiratory disease. The systems, devices, and methods discussed in this document also allow for more efficient device memory usage, such as by storing hemodynamic parameter indicative of systolic blood pressure at a respiratory phase that are clinically more relevant to diagnosis of respiratory disease. As fewer false positive detections are provided, device battery life can be extended, fewer unnecessary drugs and procedures may be scheduled, prescribed, or provided, and an overall system cost savings may be realized.

Although much of the discussion herein focuses on asthma and COPD, this is meant only by way of example. Systems and methods discussed in this document may also be suitable for monitoring patients with various sorts of acute and chronic respiratory diseases, including obstructive or restrictive lung diseases such as emphysema, COPD, pulmonary fibrosis, or sarcoidosis, among many others.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for monitoring patients with respiratory diseases. The system may detect a specified respiratory phase from a respiration signal, and generate from a hemodynamic signal one or more hemodynamic parameters correlative to at least one of a systolic blood pressure, a blood volume, or a cardiac dimension. The system may detect a restrictive or obstructive respiratory condition when the hemodynamic signal metric indicates hemodynamic deterioration during inspiration phase of respiration. The system may additionally classify the detected restrictive or obstructive respiratory condition into one of two or more categories, and deliver respective therapies based on the detection or the classification.

Figure 1:
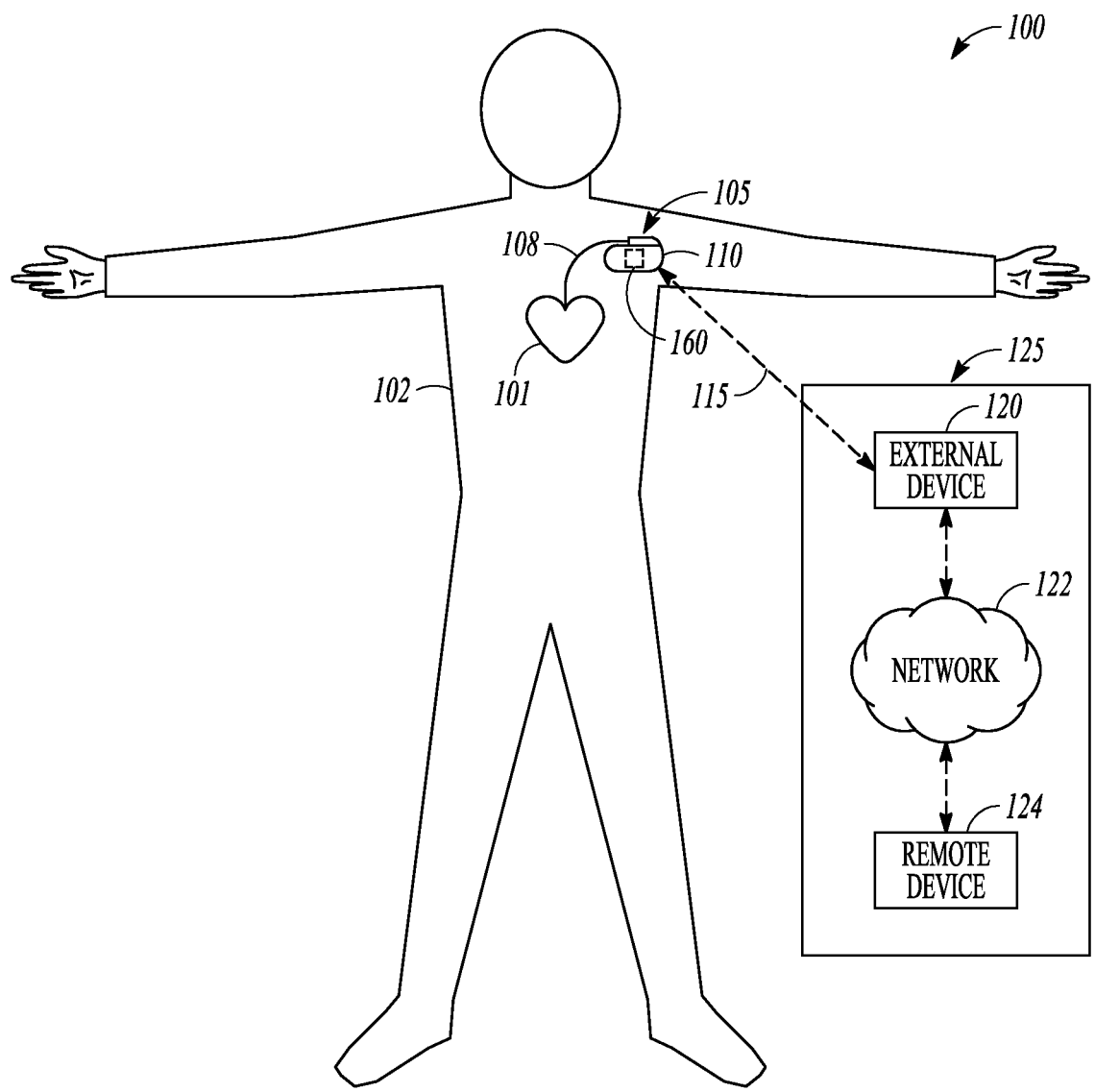
FIG. 1 illustrates generally an example of a patient management system and portions of an environment in which the patient management system may operate.

FIG. 1 illustrates generally an example of a patient management system 100 and portions of an environment in which the patient management system 100 may operate. The patient management system 100 may include an ambulatory system 105 associated with a patient body 102, an external system 125, and a telemetry link 115 providing for communication between the ambulatory system 105 and the external system 125.

The ambulatory system 105 may include an ambulatory medical device (AMD) 110 and a therapy delivery system such as a lead system 108. The AMD 110 may include an implantable device that may be implanted within the body 102 and coupled to a heart 101 via the lead system 108. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The AMD 110 may alternatively or additionally include subcutaneously implanted devices such as a subcutaneous ICD or a subcutaneous diagnostic device, wearable medical devices, or other external monitoring or therapeutic medical devices such as a bedside monitor.

The lead system 108 may include one or more transvenously, subcutaneously, or non-invasively placed leads or catheters. Each lead or catheter may include one or more electrodes. The arrangements and uses of the lead system 108 and the associated electrodes may be determined based on the patient need and the capability of the AMD 110. The lead system 108 and the associated electrodes may deliver therapy to treat cardiac or pulmonary diseases. The therapies may include pacing, cardioversion, defibrillation, neuromodulation, drug therapies, or biological therapies, among other types of therapies. In an example, the electrodes on the lead system 108 may be positioned inside or on a surface of at least a portion of the heart, such as a right atrium (RA), a right ventricle (RV), a left atrium (LA), a left ventricle (LV), or any tissue between or near the heart portions. In an example, the lead system 108 and the associated electrodes may be implanted subcutaneously or wearable on the patient body. The associated electrodes on the lead system 108 may be positioned at the patient's thorax or abdomen to sense intrinsic physiological signals indicative of cardiac or pulmonary activities, or physiological responses to diagnostic or therapeutic stimulations to a target tissue.

The AMD 110 may house an electronic circuit for sensing a physiological signal, such as by using a physiological sensor or the electrodes associated with the lead system 108. Examples of the physiological signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, RV pressure, LV coronary pressure, coronary blood temperature, blood oxygen saturation, one or more heart sounds, intracardiac acceleration, physical activity or exertion level, physiological response to activity, posture, respiration rate, tidal volume, respiratory sounds, body weight, or body temperature. The AMD 110 may initiate or adjust therapies based on the sensed physiological signals.

The patient management system 100 may include a respiratory monitor 160 for monitoring patient respiration. The respiratory monitor 160 may analyze the diagnostic data such as acquired by the ambulatory system 105 for patient monitoring, risk stratification, and detection of events indicating presence, onset, termination, improvement, or worsening of a target respiratory condition. Examples of the respiratory conditions may include wheezing, asthma, bronchoconstriction, chronic obstructive pulmonary disease (COPD), bronchiectasis, acute bronchitis, pulmonary fibrosis, pneumoconiosis, acute respiratory distress syndrome, or sleep apnea. In some examples, the respiratory monitor 160 may detect restrictive or obstructive respiratory conditions when the detected physiological signal indicates hemodynamic deterioration during a specified respiratory phase. By way of non-limiting example and as illustrated in FIG. 1, the respiratory monitor 160 may be substantially included in the AMD 110. Alternatively, the respiratory monitor 160 may be substantially included in the external system 125, or be distributed between the ambulatory system 105 and the external system 125.

The external system 125 may be used to program the AMD 110. The external system 125 may include a programmer, or a patient management system that may access the ambulatory system 105 from a remote location and monitor patient status and/or adjust therapies. By way of non-limiting example, the external system 125 may include an external device 120 in proximity of the AMD 110, a remote device 124 in a location relatively distant from the AMD 110, and a telecommunication network 122 linking the external device 120 and the remote device 124. The telemetry link 115 may be an inductive telemetry link, a capacitive telemetry link, or a radio-frequency (RF) telemetry link. The telemetry link 115 may provide for data transmission from the AMD 110 to the external system 125. This may include, for example, transmitting real-time physiological data acquired by the AMD 110, extracting physiological data acquired by and stored in the AMD 110, extracting patient history data such as data indicative of occurrences of arrhythmias, occurrences of decompensation, and therapy deliveries recorded in the AMD 110, and extracting data indicating an operational status of the AMD 110 (e.g., battery status and lead impedance). The telemetry link 115 may also provide for data transmission from the external system 125 to the AMD 110. This may include, for example, programming the AMD 110 to perform one or more of acquiring physiological data, performing at least one self-diagnostic test (such as for a device operational status), analyzing the physiological data to generate respiratory diagnostics such as presence or worsening of a target respiratory condition, or delivering at least one therapy to treat a respiratory disease.

Portions of the AMD 110 or the external system 125 may be implemented using hardware, software, or any combination of hardware and software. Portions of the AMD 110 or the external system 125 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
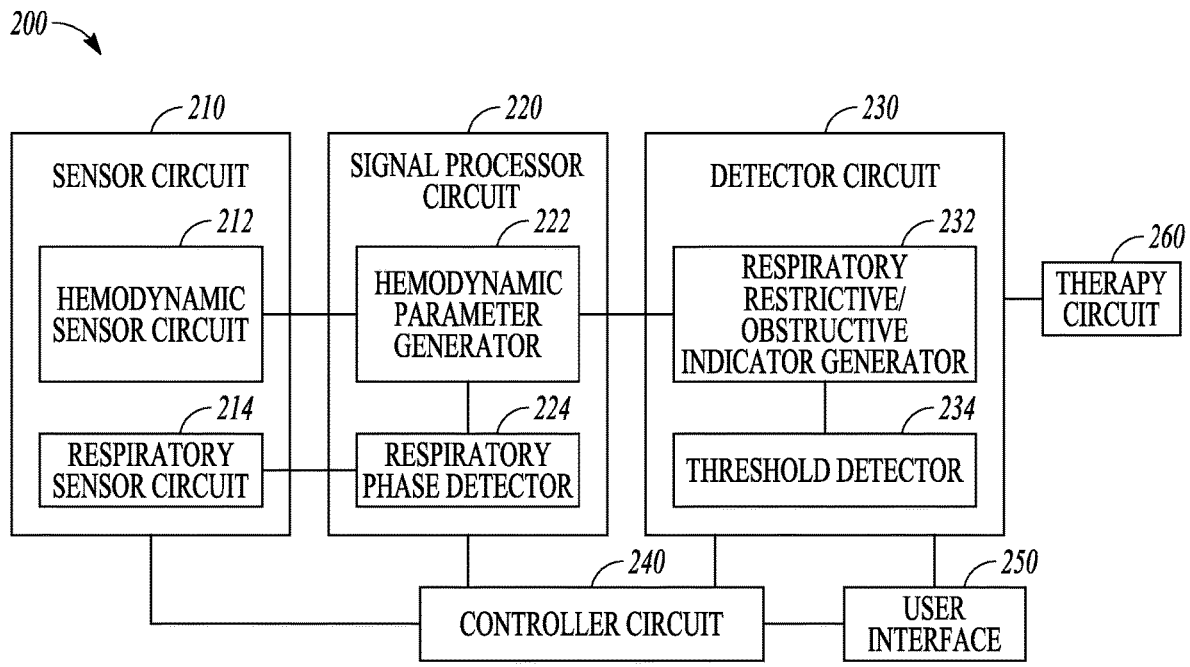
FIG. 2 illustrates generally an example of a respiratory monitoring system for monitoring respiration and detecting restrictive or obstructive respiratory conditions.

FIG. 2 illustrates generally an example of a respiratory monitoring system 200 for monitoring respiration and detecting restrictive or obstructive respiratory conditions, such as wheezing, asthma, bronchoconstriction, COPD, bronchiectasis, acute bronchitis, pulmonary fibrosis, pneumoconiosis, acute respiratory distress syndrome, or sleep apnea. The respiratory monitoring system 200 may include one or more of a sensor circuit 210, a signal processor circuit 220, a detector circuit 230, a controller circuit 240, and a user interface 250. In some examples, the respiratory monitoring system 200 may additionally include a therapy circuit 260 configured to deliver therapy to the patient to treat a respiratory disease or to prevent worsening of a restrictive or obstructive respiratory condition. At least a portion of the respiratory monitoring system 200 may be implemented within the AMD 110, distributed between two or more implantable or wearable medical devices, or distributed between the AMD 110 and the external system 125.

The sensor circuit 210 may include a hemodynamic sensor circuit 212 and a respiratory sensor circuit 214. The hemodynamic sensor circuit 212 may be configured to sense a hemodynamic status of the patient. The hemodynamic sensor circuit 212 may be coupled, through wired or wireless link, to a hemodynamic sensor deployed on or inside the patient's body. The hemodynamic sensor may include implantable, wearable, holdable, or otherwise ambulatory physiologic sensors that directly or indirectly measures dynamics of the blood flow in the heart chambers or in the blood vessels. Examples of the hemodynamic sensor and the physiologic variables to sense may include pressure sensors configured for sensing arterial pressure, pulmonary artery pressure, left atrial pressure, RV pressure, LV coronary pressure; impedance sensors configured for sensing thoracic impedance or cardiac impedance; temperature sensor configured for sensing blood temperature; accelerometers or microphones configured for sensing one or more heart sounds; optical sensors such as pulse oximeters configured for sensing blood oxygen saturation; chemical sensors configured for sensing central venous pH value or oxygen or carbon dioxide level in the blood or other tissues or organs in the body. Examples of hemodynamic sensor circuit 230 are described below, such as with reference to FIG. 3.

The respiratory sensor circuit 214 may be coupled to an implantable, wearable, holdable, or otherwise ambulatory respiratory sensor including one of an accelerometer, a microphone, an impedance sensor, or a flow sensor. The respiratory sensor circuit 214 may sense a respiration signal and detect one or more respiration parameters such as one or more of a tidal volume, a respiration rate, a minute ventilation, a respiratory sound, or a rapid-shallow breathing index (RSBI) computed as a ratio of a respiratory rate measurement to a tidal volume measurement.

The respiration signal and the hemodynamic signals may be sensed simultaneously, and the sensing of the at least one hemodynamic signal may be synchronized to the sensing of the respiration signal. In an example, a response delay between the hemodynamic sensor circuit 212 and the respiratory sensor circuit 214 may be determined such as by using synchronization pulse. Such a system delay may be attributed to a system delay due to different responsiveness of the hemodynamic sensor and the respiratory sensor, and/or a physiological delay between the respiration and the hemodynamic responses modulated by the respiration. The synchronization of the hemodynamic signal to the respiration signal may include adjusting the timings of the hemodynamic signal based on the response delay between the hemodynamic sensor circuit 212 and the respiratory sensor circuit 214.

The signal processor circuit 220 may include a hemodynamic parameter generator 222 and a respiratory phase detector 224. The hemodynamic parameter generator 222, coupled to the hemodynamic sensor circuit 212, may generate one or more hemodynamic parameters from at least one hemodynamic signal. The hemodynamic parameters may be correlative to at least one of a systolic blood pressure, a blood volume, or a cardiac dimension. The hemodynamic parameters may include statistical measurements derived from a plurality of measurements of the physiologic variables, such as mean, median or other central tendency measures, or second order statistics including variance or standard deviation of the measurements, a histogram of the hemodynamic parameter intensity, or higher order statistics of the measurements. Alternatively or additionally, the hemodynamic parameter generator 222 may generate a hemodynamic parameter using one or more signal trends of the physiologic parameter (such as intensity of the physiologic parameter over time), one or more signal morphological descriptors, or signal power spectral density at a specified frequency range. Examples of the hemodynamic parameter may include a heart rate, a cardiac or thoracic pressure metric, a LV or RV systolic volume, diastolic volume, or stroke volume metric, a cardiac output metric, cardiac timing intervals such has systolic or diastolic timing interval, LV ejection time, echocardiographic metric such as a ratio of early to late ventricular filling velocities (E/A ratio) including a trans-mitral or trans-tricuspid E/A ratios, a cardiac or thoracic impedance metric, or a photo plethysmography metric, among others.

The respiratory phase detector 224 may be coupled to the respiratory sensor circuit 214 to detect from the respiration signal a respiratory phase within a respiratory cycle. Examples of the respiratory phase may include an inspiration phase, an expiration phase, an apneic phase, a hypopneic phase, a transitional phase from inspiration to expiration, or a transitional phase from expiration to inspiration. The respiratory phase may include a specified portion of the inspiration, expiration, or transitional phase of respiration with respect to a reference time of respiration, such as end of inspiration or end of expiration.

The detector circuit 230, coupled to the signal processor circuit 220, may include a respiratory restriction/obstruction indicator generator 232 to generate an indication of status of a restrictive or obstructive respiratory condition, such as presence, onset, termination, improvement, or worsening of a restrictive or obstructive respiratory condition. In an example, the respiratory restriction/obstruction indicator may be computed using one or more hemodynamic parameters measured during a specified respiratory phase, such as at least a portion of the inspiration phase. The detector circuit 230 may include a threshold detector 234 to detect if respiratory restriction/obstruction indicator exceeds a specified threshold, and a diagnostic of respiratory disease may be generated.

One or more of the signal processor circuit 220 or the detector circuit 230 may be implemented as a part of a microprocessor circuit. The microprocessor circuit may be a dedicated processor such as a digital signal processor, application specific integrated circuit (ASIC), microprocessor, or other type of processor for processing information including the physiological signals received from the sensor circuit 210. Alternatively, the microprocessor circuit may be a general purpose processor that may receive and execute a set of instructions of performing the functions, methods, or techniques described herein.

The signal processor circuit 220 or the detector circuit 230 may include circuit sets comprising one or more other circuits or sub-circuits. These circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The controller circuit 240 may control the operations of the sensor circuit 210, the signal processor circuit 220, the detector circuit 230, the user interface 250, and the data and instruction flow between these components. The user interface 250 may include an output unit to generate a human-perceptible presentation of diagnostic information, such as a display of the respiratory restriction/obstruction indicator. The output unit may generate an alert if the respiratory restriction/obstruction indicator indicates presence of a new episode of asthma attack or COPD, or worsening of an existing respiratory disease. The output unit may also display information including the hemodynamic signals and the respiration signals, or trends of a hemodynamic parameter over time. The information may be presented in a table, a chart, a diagram, or any other types of textual, tabular, or graphical presentation formats, for displaying to a system user. The presentation of the output information may include audio or other human-perceptible media format. The output unit may provide the respiratory restriction/obstruction indicator to another process such as to assess patient health status or to recommend or titrate a therapy. The user interface 250 may also include input device such as a keyboard, on-screen keyboard, mouse, trackball, touchpad, touchscreen, or other pointing or navigating devices. The input device may enable a system user such as a clinician to program the parameters used for sensing the hemodynamic signals, generating trends of hemodynamic parameters, or generating the respiratory restriction/obstruction indicator for detecting the target respiratory condition. In an example, at least a portion of the user interface 250 may be implemented in the external system 125.

In some examples, the respiratory monitoring system 200 may additionally include a therapy circuit 260 that is configured to deliver a therapy to the patient. The therapy may be triggered by a command signal in response to the respiratory restriction/obstruction indicator satisfying a specified condition. Examples of the therapy may include electrostimulation therapy delivered to cardiac or pulmonary tissue, heart, a nerve tissue, other target tissues in response to the detection of the target physiological event, or drug therapy including delivering drug to a tissue or organ. In some examples, therapy circuit 260 may be adjust an existing therapy based at least on the respiratory restriction/obstruction indicator, such as adjusting a stimulation parameter or drug dosage.

Figure 3:
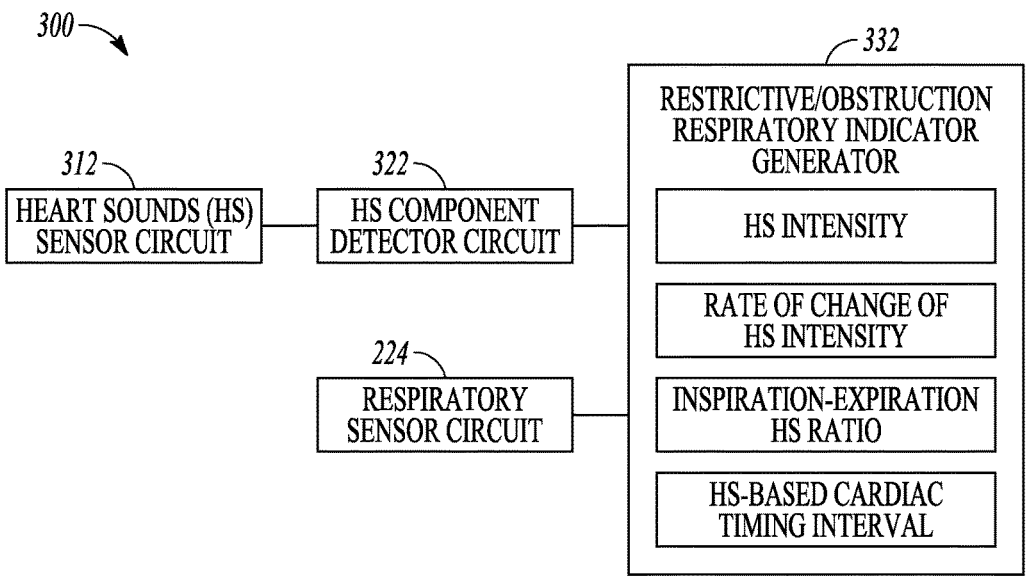
FIG. 3 illustrates generally an example of a portion of a system for generating restrictive or obstructive respiratory indicator using heart sounds signal.

FIG. 3 illustrates generally an example of a portion of a system 300 for generating restrictive or obstructive respiratory indicator using heart sounds signal. The system portion 300 may be an embodiment of corresponding portions of the respiratory monitoring system 200. The system portion 300 may include a heart sounds (HS) sensor circuit 312 which may be an embodiment of the hemodynamic sensor circuit 212, and a HS component detector circuit 322 which may be an embodiment of the hemodynamic parameter generator 222.

The HS sensor circuit 312 may sense HS information indicative of acoustic or mechanical activity of a heart. The HS information may include information of at least one HS component, such as first (S1), second (S2), third (S3), or fourth (S4) heart sound. In an example, the HS waveform may include at least one ensemble average of a HS signal over multiple physiological cycles such as multiple cardiac cycles, or over a specified time period such as one minute, ten minutes, one hour, one day, etc. The HS sensor circuit 312 may be coupled to one or more physiologic sensors that may sense, detect, or otherwise obtain HS information from a subject. Such physiologic sensors, referred to as "HS sensors", may be an implantable, wearable, holdable, or otherwise ambulatory sensor, and placed external to the patient or implanted inside the body. Examples of the HS sensor may include an accelerometer, an acoustic sensor, a microphone, a piezo-based sensor, or other vibrational or acoustic sensors may also be used to sense the HS signal. The HS sensor may be included in at least one part of an ambulatory system, such as the AMD 110, or a lead coupled to the ambulatory medical device.

The HS component detector circuit 322 may pre-process a sensed HS signal, including amplification, digitization, filtering, or other signal conditioning operations. In an example, the signal sensor circuit 210 may include a band-pass filter adapted to filter the received HS signal to a frequency range of approximately between 5 and 90 Hz, or approximately between 9 and 90 Hz. In an example, the signal sensor circuit 210 may include a double or higher-order differentiator configured to calculate a double or higher-order differentiation of the received HS signal.

The HS component detector circuit 322 may further detect, using the processed HS signal, one or more HS components including S1, S2, S3 or S4 heart sounds. In an example, the HS component detector circuit 322 may generate respective time windows for detecting one or more HS components. The time windows may be determined with reference to a physiologic event such as Q wave, R wave, or QRS complexes detected from a surface ECG, a subcutaneous ECG, or cardiac sensing events in an intracardiac EGM. For example, an S1 detection window may begin at 50 milliseconds (msec) following a detected R wave and have a duration of 300 msec. An S2 detection window may begin at specified offset following a detected R wave or S1 heart sound. An S3 detection window may be determined using at least one cardiac signal feature such as the R-wave timing or the timing of S2 heart sound. The S3 detection window may have a specified duration and may begin at a specified offset following the detected S2. In an example, the offset may be 125 msec, and the S3 window duration may be 125 msec. The offset or the S3 window duration may be a function of a physiologic variable such as a heart rate. For example, the offset may be inversely proportional to the heart rate, such that the S3 detection window may start at a smaller offset following the S2 at a higher heart rate.

The HS component detector circuit 322 may detect an HS component from at least a portion of the HS signal within the respective HS detection window. In an example, HS signal energy within a S2 detection window may be computed and compared to a S2 energy threshold, and an S2 component is detected in response to the HS signal energy exceeds the S2 energy threshold. In an example, the HS component detector circuit 322 may detect an HS component adaptively by tracking the temporal locations of the previously detected HS features. For example, an S3 heart sound may be detected by adaptively tracking the timing of historically detected S3 heart sounds. A dynamic programming algorithm may be used to detect and track the S3 heart sound within the S3 detection window, such as that disclosed in the commonly assigned Patangay et al. U.S. Pat. No. 7,853,327 entitled "HEART SOUND TRACKING SYSTEM AND METHOD," which is hereby incorporated by reference in its entirety.

The restrictive/obstructive respiratory indicator generator 332, coupled to the HS component detector circuit 322 and the respiratory phase detector 224, may generate an indicator of the respiratory restriction or obstruction using the HS components synchronized with a specified respiratory phase, such as one or more of S1, S2, S3 or S4 heart sounds during an inspiration phase of the respiration signal. In a characteristic phenomenon of paradoxical pulse, a reduced systolic pressure during inspiration may be indicative of abnormal restriction or obstruction in the respiratory system. An increase in S1 heart sound intensity or a decrease in S2 heart sound intensity during inspiration may be correlative to a reduced systolic pressure during inspiration, and may be used to detect abnormal respiratory restriction or obstruction such as asthma attack or worsening of an existing respiratory disease. In an example, the restrictive/obstructive respiratory indicator may include intensity of an S1 heart sound (∥S1∥) or intensity of S2 heart sound (∥S2∥) during an inspiration phase. Examples of the intensity of a HS component may include amplitude of a detected HS component in a time-domain HS signal, a filtered HS single, a transformed HS signal such as integrated HS energy signal or differentiated HS signal, peak value of the power spectral density, or peak value of a generic measurement within the respective HS detection window, such as peak envelop signal or root-mean-squared value of the portion of the HS signal within the HS detection window. The threshold detector 234 may detect presence of a restrictive or obstructive respiratory condition if ∥S1∥ during inspiration exceeds a specified threshold, or if ∥S2∥ during an inspiration phase falls below a specified threshold. In some examples, the restrictive/obstructive respiratory indicator may include a rate of change of ∥S1∥ or a rate of change of ∥S2∥ during an inspiration phase. The threshold detector 234 may detect presence of a restrictive or obstructive respiratory condition if a rate of increase of ∥S1∥ or a rate of decrease of ∥S2∥ during inspiration exceeds a specified threshold.

In an example, the restrictive/obstructive respiratory indicator may include a heart sound component during a first respiration phase relative to the heart sound component during a different second respiration phase. Examples of the relative measures at different respiratory phases may include a ratio of ||S1|| during inspiration to ||S1|| during expiration (denoted by $\|S1\|_{Insp}/\|S1\|_{Exp}$), or a ratio of ||S2|| during inspiration to ||S2|| during expiration (denoted by $\|S2\|_{Insp}/\|S2\|_{Exp}$). The threshold detector 234 may detect presence of a restrictive or obstructive respiratory condition if the ratio $\|S1\|_{Insp}/\|S1\|_{Exp}$ exceeds a specified threshold, or if the ratio $\|S2\|_{Insp}/\|S2\|_{Exp}$ falls below a specified threshold.

One or more of S1, S2, S3 or S4 heart sounds may be sensed from an ensemble average of the HS signals during certain phase of the respiratory cycle over multiple respiratory cycle. The ensemble-averaged HS signals synchronized to respiratory phase may have a higher signal-to-noise ratio, and thus a more reliable estimate of the heart sound intensities. In an example, the inspiration phase of the respiratory cycle may be broken down into a plurality of bins, denoting successive sub-phases of inspiration. Heart sounds such as S1 or S2 occurring within a particular bin over a plurality of respiratory cycles may be ensemble-averaged to obtain a less noisy estimate of S1 corresponding to the respiratory phase represented by the particular bin. Ensemble averaging of heart sounds based on respiratory phase, such as that disclosed in the commonly assigned Stahmann et al. U.S. Pat. No. 8,096,954 entitled "ADAPTIVE SAMPLING OF HEART SOUNDS," is hereby incorporated by reference in its entirety.

In some examples, the HS component detector circuit 322 may further generate a composite HS parameter including a relative intensity between one of the S1, S2, S3, or S4 heart sound and another of the S1, S2, S3, or S4 heart sound, during a specified respiration phase. The restrictive/obstructive respiratory indicator generator 322 may generate a restriction or obstruction indicator ||S1||/||S2||, or a rate of change of ||S1||/||S2||. The threshold detector 234 may detect presence of a restrictive or obstructive respiratory condition if the ratio ||S1||/||S2||, or a rate of increase in ||S1||/||S2||, exceeds a respective threshold.

In some examples, the HS component detector circuit 322 may alternatively or additionally generate a HS-based cardiac timing interval (CTI) using the sensed cardiac electrical activity and the detected HS component. The CTI represents the timing interval between two cardiac events such as a cardiac electrical event detected from the cardiac electrical signal and a mechanical event such as detected from a cardiac mechanical signal or a hemodynamic signal such as heart sound signal. The CTI may include a pre-ejection period (PEP), a systolic timing interval (STI), a left-ventricular ejection time (LVET), or a diastolic timing interval (DTI), among others. The PEP represents the total duration of the electrical and mechanical events prior to ejection, and may be measured as the time duration from the onset of the QRS to the S1 heart sound, that is, PEP≈Q–S1 interval, or from the ventricular pacing (Vp) signal to the beginning of ventricular ejection such as represented by the onset of S1 heart sound, that is, PEP≈Vp–S1 interval. LVET may be measured as the period from S1 to S2 heart sounds. The STI represents the duration of total electro-mechanical systole, and may be measured as the interval from the onset of the QRS complex on the ECG or the atrial activation event in an intracardiac EGM to the S2 heart sound, that is, STI≈Q–S2 interval, or from the ventricular pacing (Vp) signal to the end of ventricular ejection such as represented by the onset of S2 heart sound, that is, STI≈Vp–S2 interval. The DTI represents the duration of total electro-mechanical diastole, and may be measured as the interval from the S2 heart sound to the onset of the QRS complex on the ECG or the atrial activation event in an intracardiac EGM of the next cardiac cycle, that is, DTI≈S2–Q interval. In various examples, the CTI may include composite measures using two or more of the STI, the DTI, the PEP, the cardiac cycle (CL), or the LVET. Examples of the composite measures may include PEP/LVET ratio, STI/DTI ratio, STI/CL ratio, or DTI/CL ratio, among others.

The restrictive/obstructive respiratory indicator generator 322 may generate a restriction or obstruction indicator using one or more of the CTI measurements, or a rate of change of the CTI measurements. The threshold detector 234 may detect presence of a restrictive or obstructive respiratory condition if the CTI or the rate of change of CTI satisfies a specified condition. For example, if PEP/LVET during inspiration exceeds a specified threshold, or if a relative measure (such as a difference) between PEP/LVET during inspiration with respect to PEP/LVEP during expiration exceeds a specified threshold, then a restrictive or obstructive respiratory condition may be deemed detected.

Figure 4:
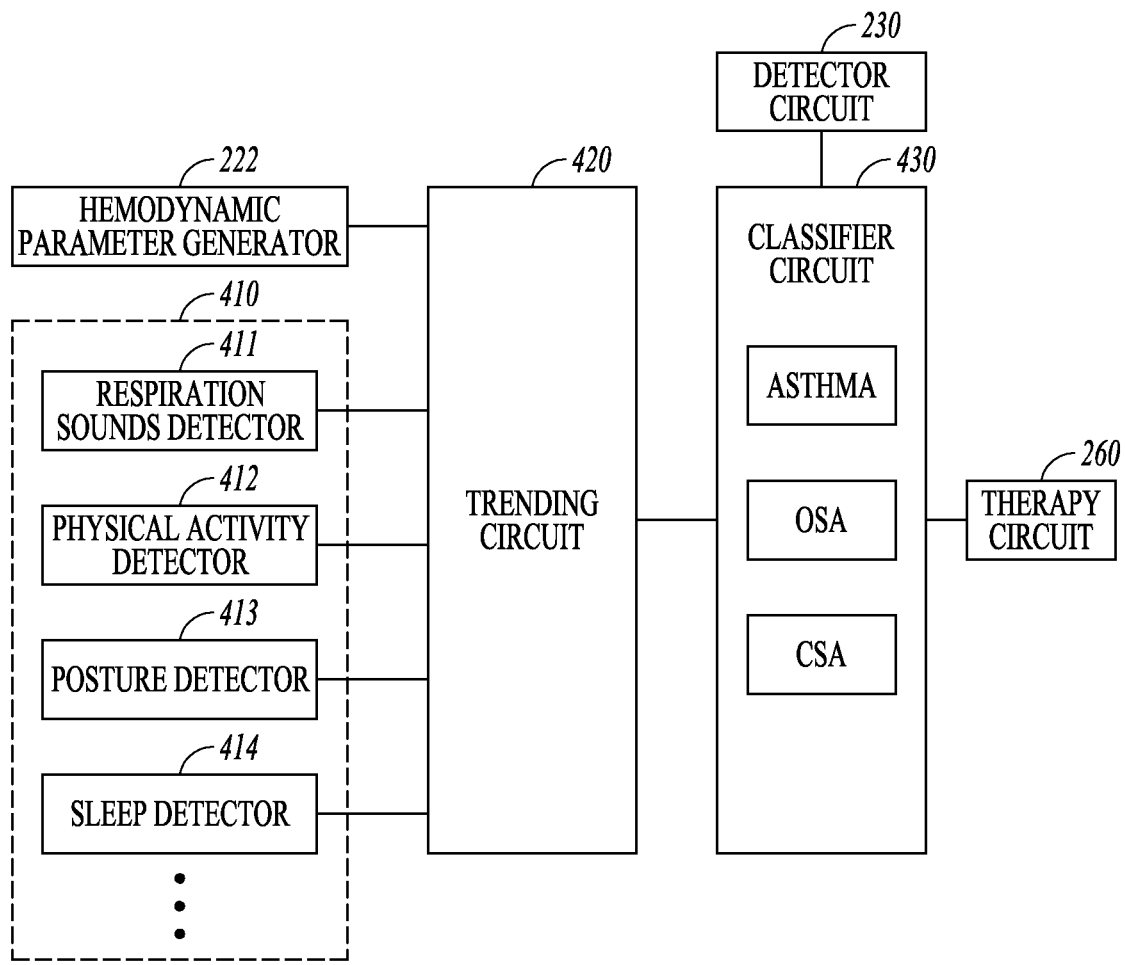
FIG. 4 illustrates generally an example of a portion of a system for distinguishing among various restrictive or obstructive respiratory conditions.

FIG. 4 illustrates generally an example of a portion of a system 400 for distinguishing among various restrictive or obstructive respiratory conditions. The system 400 may be used to classify the restrictive or obstructive respiratory condition detected by the respiratory monitoring system 200 or any embodiment thereof. The system portion 400 may be a portion of the respiratory monitoring system 200. Alternatively, the system portion 400 may be implemented in a separate device than the respiratory monitoring system 200, such as within the external system 125.

The system portion 400 may include a trending circuit 420 coupled to the hemodynamic parameter generator 222 and one or more physiological detectors 410 each configured to detect a physiological parameter. The physiological parameters detected by the physiological detectors 410 may be different from the hemodynamic parameters produced by the hemodynamic parameter generator 222, and may be used to distinguish various types of restrictive or obstructive respiratory conditions. By way of non-limiting example and as illustrated in FIG. 4, the physiological detectors 410 may include one or more of a respiratory sounds detector 411, a physical activity detector 412, a posture detector 413, or a sleep detector 414, among others. The respiratory sounds detector 411 may be coupled to one or more implantable, wearable, holdable, or other ambulatory physiological sensors disposed at the patient's thorax or abdomen to sense a signal indicative of respiratory sounds. The respiratory sounds may include one or more of lung sounds, tracheal sounds, or bronchial sounds, among others. Examples of the physiological sensors for sensing the physiological signal indicative of respiratory sounds may include accelerometers, microphone sensors, pressure sensors, flow sensors, impedance sensors, respiration sensors, temperature sensors, or chemical sensors, among others. In some examples, the detector circuit 230 or any variant thereof may detect the restrictive or obstructive respiratory condition further using the respiratory sound.

The physical activity detector 412 may be coupled to a wearable or implantable accelerometer to detect one or more of activity intensity or activity duration. The accelerometer may be single-axis or multi-axis accelerometer, and may sense an acceleration signal of at least a portion of a subject's body. The strength of the acceleration signal may be indicative of the physical activity level. The posture detector 413 may be coupled to a wearable or implantable posture sensor to detect a posture or position of the patient. Examples of the posture sensor may include a tilt switch, a single axis accelerometer, or a multi-axis accelerometer, among others. The posture sensor may be disposed external to the body or implanted inside the body. Posture may be represented by, for example, a tilt angle. In some examples, posture or physical activity information may be derived from thoracic impedance information. The sleep detector 414 may be coupled to one or more sensors to detect accelerometer, piezoelectric sensor, biopotential electrodes and sensors, or other physiologic sensors to detect the posture, change of posture, activity, respiration, heart rate, electroencephalograms, or other signals indicative of a sleep or awake state.

The trending circuit 420 may track the temporal changes of one or more hemodynamic parameters produced by the hemodynamic parameter genera ore 222 and the temporal changes of the one or more physiological parameters detected from the physiological detectors 410. In an example, the trending circuit 420 may generate a trend of respiratory sounds intensity or a trend of spectral content of the respiratory sounds within a specified frequency range. The trending circuit 420 may generate one or more trends over time of non-hemodynamic parameters such as a trend of physical activities, posture states, or sleep or awake states.

The classifier circuit 430 may be coupled to detector circuit 230 and the trending circuit 420, and use the trends of hemodynamic parameters or additionally with the trends of non-hemodynamic parameters to classify the detected restrictive or obstructive respiratory condition into one of two or more categories of restrictive or obstructive respiratory diseases including wheezing, asthma, bronchoconstriction, chronic obstructive pulmonary disease, bronchiectasis, acute bronchitis, pulmonary fibrosis, pneumoconiosis, acute respiratory distress syndrome, or sleep apnea. In an example, the classifier circuit 430 performs classification in response to the detector circuit 230 producing a detection signal of the restrictive or obstructive respiratory condition.

The classifier circuit 430 may discriminate an asthma from an obstructive sleep apnea (OSA) using at least the trended one or more physiological parameters. In an example, in response to the detection of the restrictive or obstructive respiratory condition, a heart rate trend may be generated. Asthma may typically occur when the patient is awake and characterized by rapid heart rate which may be due to higher adrenaline level. OSA may typically occur during sleep and is associated with lower heart rate. The classifier circuit 430 may classify the restrictive or obstructive respiratory condition as asthma if the trended heart rate exceeds a threshold, or as OSA if the heart rate falls below a threshold. In another example, classifier circuit 430 may classify the restrictive or obstructive respiratory condition as asthma if an upright posture is detected, or as OSA if a lying posture is detected. The classifier circuit 430 may additionally or alternatively uses trend of upper airway resistance such as measured using an impedance sensor, or electroencephalogram to distinguish asthma from OSA.

The classifier circuit 430 may discriminate a central sleep apnea (CSA) from an obstructive sleep apnea (OSA) using at least the trended one or more physiological parameters. While the phenomenon of paradoxical pulse may typically occur during OSA, episodes of CSA may not be accompanied by paradoxical pulse. The classifier circuit 430 may use the trended hemodynamic signals to distinguish OSA from CSA. For example, a detection of hemodynamic deterioration during inspiration may be more likely an indication of OSA than CSA. As previously discussed with reference to FIG. 4, heart sounds such as S1 or S2 heart sounds may be correlated to arterial pressure change during inspiration. An OSA may be declared if an increasing trend of ||S1|| or a decreasing trend of ||S2|| is detected, or a CSA may be declared if no such an increase in ||S1|| or decrease in ||S2|| in detected during inspiration. The classifier circuit 430 may additionally or alternatively distinguish CSA from OSA using the trends of intrathoracic pressure, trends of the intercostal muscle electromyogram, or trends of the diaphragm muscle electromyogram to determine the presence of hemodynamic, among other trends of the physiological parameters correlative of hemodynamic deterioration during inspiration. As illustrated in FIG. 4, the classifier circuit 430 may be coupled to the therapy circuit 260, which my deliver targeted therapy based on the classification of the restrictive or obstructive respiratory conditions.

Figure 5:
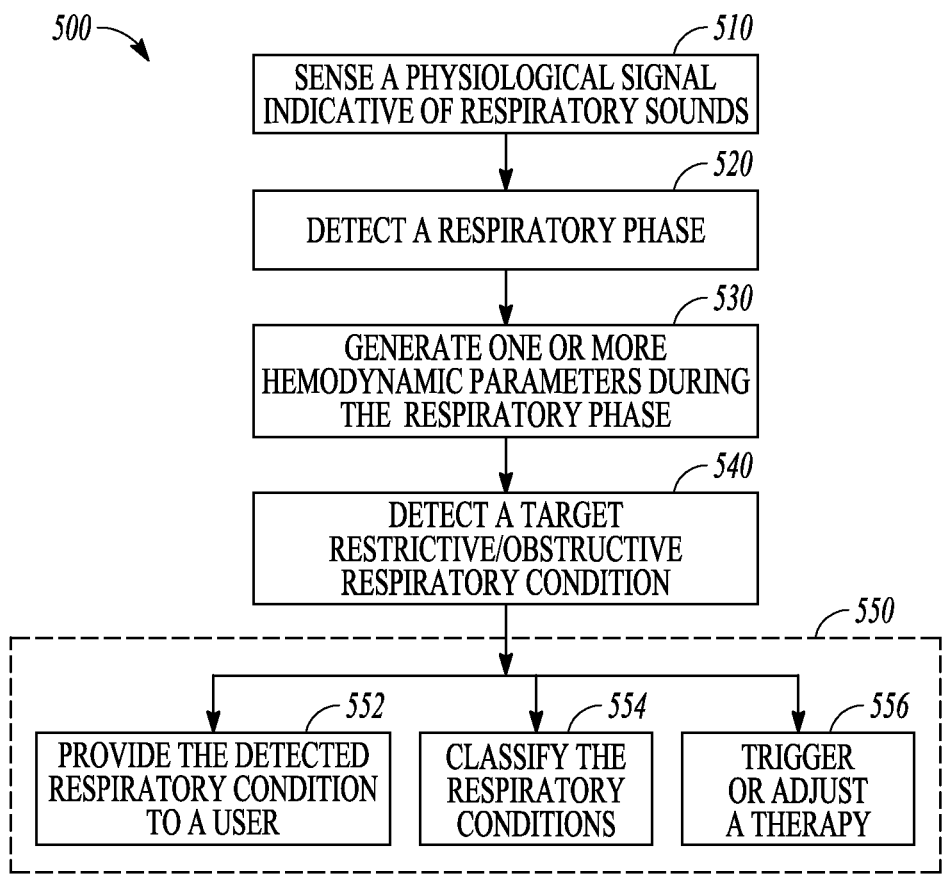
FIG. 5 illustrates generally an example of a method for monitoring respiration and detecting restrictive or obstructive respiratory conditions.

FIG. 5 illustrates generally an example of a method 500 for monitoring respiration and detecting restrictive or obstructive respiratory conditions, such as wheezing, asthma, bronchoconstriction, COPD, bronchiectasis, acute bronchitis, pulmonary fibrosis, pneumoconiosis, acute respiratory distress syndrome, or sleep apnea. The method 500 may be implemented and operate in an ambulatory medical device such as an implantable or wearable medical device, or in a remote patient management system. In an example, the method 500 may be executed by the respiratory monitor 160 or by the external system 125. In an example, the method 500 may be implemented in and executed by the respiratory monitoring system 200 or any embodiments thereof.

The method 500 begins at 510 by sensing one or more physiological signals from a patient, including a respiration signal and at least one hemodynamic signal. The respiration signal may be sensed using an implantable, wearable, holdable, or otherwise ambulatory respiratory sensor, including one of an accelerometer, a microphone, an impedance sensor, or a flow sensor. The hemodynamic signal may be sensed using one or more implantable or wearable hemodynamic sensors, which may include pressure sensors configured for sensing arterial pressure, pulmonary artery pressure, left atrial pressure, RV pressure, LV coronary pressure; impedance sensors configured for sensing thoracic impedance or cardiac impedance; temperature sensor configured for sensing blood temperature; accelerometers or microphones configured for sensing one or more heart sounds; optical sensors such as pulse oximeters configured for sensing blood oxygen saturation; chemical sensors configured for sensing central venous pH value or oxygen or carbon dioxide level in the blood or other tissues or organs in the body, among others. The sensing of the at least one hemodynamic signal may be synchronized to the sensing of the respiration signal, such as by adjusting the timings of the hemodynamic signal based on a response delay between the hemodynamic sensing circuit and the respiratory sensing circuit.

At 520 a respiratory phase within a respiratory cycle may be detected from the respiratory signal. Examples of the respiratory phase may include an inspiration phase, an expiration phase, an apneic phase, a hypopneic phase, a transitional phase from inspiration to expiration, or a transitional phase from expiration to inspiration. The respiratory phase may include a specified portion of the inspiration, expiration, or transitional phase of respiration with respect to a reference time of respiration, such as end of inspiration or end of expiration.

At 530, one or more hemodynamic parameters may be generated from the one hemodynamic signals during a specified respiratory phase. The hemodynamic parameters may be correlative to at least one of a systolic blood pressure, a blood volume, or a cardiac dimension. The hemodynamic parameters may include statistical or morphological parameters extracted from the hemodynamic signals. Examples of the hemodynamic parameter may include a heart rate, a cardiac or thoracic pressure metric, a LV or RV systolic volume, diastolic volume, or stroke volume metric, a cardiac output metric, cardiac timing intervals such has systolic or diastolic timing interval, LV ejection time, echocardiographic metric such as a ratio of early to late ventricular filling velocities (E/A ratio) including a trans-mitral or trans-tricuspid E/A ratios, a cardiac or thoracic impedance metric, or a photo plethysmography metric, among others.

At 540, a target restrictive or obstructive respiratory condition may be detected in response to the one or more hemodynamic parameters satisfying a specified condition during the detected respiratory phase. The target respiratory condition may include presence, onset, termination, improvement, or worsening of a restrictive or obstructive respiratory condition. A respiratory restriction/obstruction indicator may be computed using one or more hemodynamic parameters measured during a specified respiratory phase, such as at least a portion of the inspiration phase. If the respiratory restriction/obstruction indicator exceeds a specified threshold, a diagnostic of respiratory disease may be generated.

In an example, the detection of the target restrictive or obstructive respiratory condition at 540 may include a detection of a hemodynamic deterioration from the one or more hemodynamic parameters during at least a portion of an inspiration phase. Respiratory disorders such as asthma attack or worsening of COPD may cause abnormal restriction or obstruction in the respiratory system. This in turn may produce a phenomenon of paradoxical pulse characterized by hemodynamic changes during respiration that includes an abnormally higher systolic blood pressure during inspiration than during expiration. The hemodynamic parameters obtained during the inspiration phase such as generated at 530, which may be correlated to the systolic pressure change during inspiration, may be compared to a threshold to determine the presence of paradoxical pulse, and be used to detect the target restrictive or obstructive respiratory condition.

At 550, the detected restrictive or obstructive respiratory condition may be provided to a user or a process. At 552, a human-perceptible presentation of the respiratory restriction/obstruction indicator or the detection decision of the target restrictive or obstructive respiratory condition may be generated, and displayed such as on the user interface 250. The information may be presented in a table, a chart, a diagram, or any other types of textual, tabular, or graphical presentation formats. An alert may be generated in response to the respiratory restriction/obstruction indicator satisfying a specified condition, such as exceeding an alert threshold.

At 554, the detection of the restrictive or obstructive respiratory condition may be used to trigger a classification of the detected respiratory condition into one of two or more categories of the restrictive or obstructive respiratory conditions, including wheezing, asthma, bronchoconstriction, chronic obstructive pulmonary disease, bronchiectasis, acute bronchitis, pulmonary fibrosis, pneumoconiosis, acute respiratory distress syndrome, or sleep apnea. The classification may be based on the one or more hemodynamic parameters trended over time. Additionally, the classification at 554 may include trends of other physiological parameter, such as respiratory sounds, physical activity level, posture or position of the patient, or sleep or awake state of the patient, among others. In an example, an asthma episode may be distinguished from an obstructive sleep apnea (OSA) using a heart rate trend, where an asthma episode is detected if the trended heart rate exceeds a threshold, or an OSA is detected if the heart rate falls below a threshold. Alternatively, the classification may be based on posture sensor trend, where an asthma episode is detected if an upright posture is detected, or as OSA is detected if a lying posture is detected. In another example, a central sleep apnea (CSA) may be distinguished from an obstructive sleep apnea (OSA) using heart sounds parameters. While the phenomenon of paradoxical pulse may typically occur during OSA, episodes of CSA may not be accompanied by paradoxical pulse. An OSA may be declared if an increasing trend of $\|S1\|$ or a decreasing trend of $\|S2\|$ is detected, or a CSA may be declared if no such an increase in $\|S1\|$ or decrease in $\|S2\|$ in detected during inspiration.

At 556, the detection of the restrictive or obstructive respiratory condition or the classification of the respiratory conditions may be used to trigger a therapy delivered to the patient. Examples of the therapy may include electrostimulation therapy delivered to the heart, a nerve tissue, other target tissues in response to the detection of the target physiological event, or drug therapy including delivering drug to a tissue or organ. In some examples, the detection or the classification of the restrictive or obstructive respiratory condition may be used to modify an existing therapy, such as to adjust a stimulation parameter or drug dosage.

Figure 6:
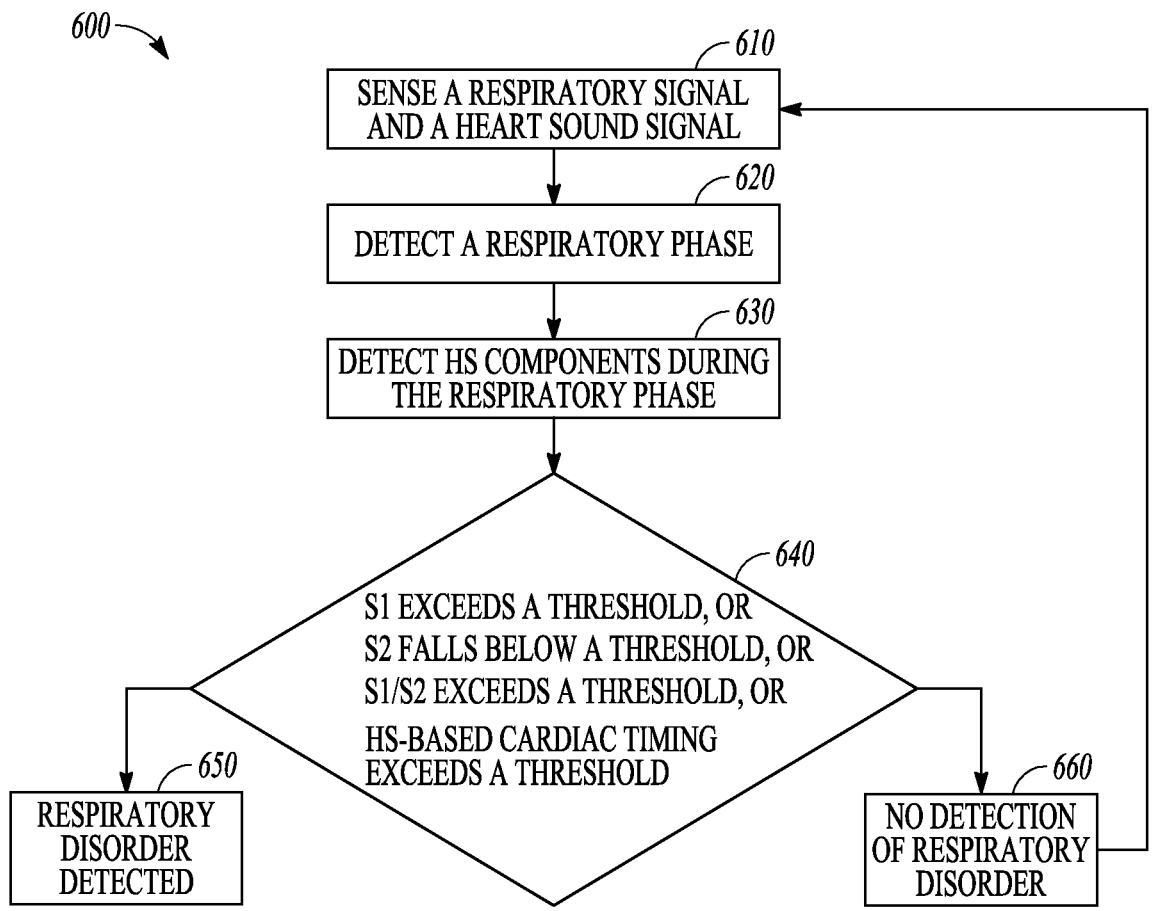
FIG. 6 illustrates generally an example of a method for detecting restrictive or obstructive respiratory conditions using heart sounds.

FIG. 6 illustrates generally an example of a method 600 for detecting restrictive or obstructive respiratory conditions using heart sounds. The method 600 may be executed by the respiratory monitor 160 or by the external system 125. In an example, the method 500 may be implemented in and executed by the system portion 300 or any embodiments thereof.

The method 600 begins at 610 by sensing a respiratory signal and a heart sound (HS) signal. The HS signal may be sensed using an implantable, wearable, holdable, or otherwise ambulatory HS sensor such as an accelerometer, an acoustic sensor, a microphone, a piezo-based sensor, or other vibrational or acoustic sensors. The respiration signal may be sensed using an implantable, wearable, holdable, or otherwise ambulatory respiratory sensor, as discussed at 510 of method 500 with reference to FIG. 5. The sensing of the HS signal may be synchronized to the sensing of the respiration signal, such as by adjusting the timings of the HS signal based on a response delay between the HS sensing circuitry and the respiratory sensing circuitry.

At 620, a respiratory phase within a respiratory cycle may be detected from the respiratory signal using a similar method as described at step 520 of the method 500 with reference to FIG. 5. Then, HS components may be detected at 630 during a specified respiratory phase, such as during an inspiration phase. The HS components, such as S1, S2, S3 or S4 heart sounds, may each be detected within a time window with respect to a reference time such as the Q wave or R wave on an ECG.

At 640, one or more of the heart sounds components may be compared to respective thresholds to detect hemodynamic deterioration during a specified phase of respiration, such as during inspiration. In an example, intensity a HS component, such as intensity of an S1 heart sound ($\|S1\|$) or intensity of S2 heart sound ($\|S2\|$) during an inspiration phase, may be compared to respective thresholds. An increase in $\|S1\|$ or a decrease in $\|S2\|$ during inspiration may be correlated to a reduced systolic pressure during inspiration, thus indicative of abnormal restriction or obstruction in the respiratory system, or the presence of paradoxical pulse. If $\|S1\|$ during inspiration exceeds a specified threshold, or if $\|S2\|$ during an inspiration phase falls below a specified threshold, the respiratory disorder is deemed detected at 650. The detection of restrictive/obstructive respiratory condition may alternatively or additional be based on a rate of change of $\|S1\|$ or a rate of change of $\|S2\|$ during an inspiration phase. If at 640 the rate of increase of $\|S1\|$ or a rate of decrease of $\|S2\|$ during inspiration exceeds a specified threshold, then the respiratory disorder is detected at 650. In some examples, a relative measure of heart sound intensity at different respiration phases, such as a ratio of $\|S1\|$ during inspiration to $\|S1\|$ during expiration ($\|S1\|_{Insp}/\|S1\|_{Exp}$) or a ratio of $\|S2\|$ during inspiration to $\|S2\|$ during expiration ($\|S2\|_{Insp}/\|S2\|_{Exp}$), may be used to detect respiratory disorder. A restrictive or obstructive respiratory condition is detected if the ratio $\|S1\|_{Insp}/\|S1\|_{Exp}$ exceeds a specified threshold, or if the ratio $\|S1\|_{Insp}/\|S1\|_{Exp}$ falls below a specified threshold.

The detection decision at 640 may further be based on a relative intensity between one of the S1, S2, S3, or S4 heart sound and another of the S1, S2, S3, or S4 heart sound, such as the HS intensity ratio $\|S1\|/\|S2\|$, or a rate of change of $\|S1\|/\|S2\|$. A restrictive or obstructive respiratory condition is deemed detected at 650 if the ratio $\|S1\|/\|S2\|$, or a rate of increase in $\|S1\|/\|S2\|$, exceeds a respective threshold.

The detection decision at 640 may additionally be based on a HS-based cardiac timing interval (CTI), such as one or more of a pre-ejection period (PEP), a systolic timing interval (STI), a left-ventricular ejection time (LVET), or a diastolic timing interval (DTI), among others. The PEP may be measured as the Q–S1 interval from Q wave on an ECG to S1 heart sound, or Vp–S1 interval from the ventricular pacing (Vp) signal to S1 heart sound. The LVET may be measured as the period from S1 to S2 heart sounds. The STI may be measured as Q–S2 interval from Q wave on a ECG to S2 heart sound, or Vp–S2 interval from the ventricular pacing (Vp) signal to S2 heart sound. The DTI may be measured as the S2–Q interval from the S2 heart sound to the Q wave of the next cardiac cycle.

Restrictive or obstructive respiratory condition may be detected at 640 if the CTI or the rate of change of CTI satisfies a specified condition. If at 640 the PEP/LVET during inspiration exceeds a specified threshold, or if a relative measure between PEP/LVET during inspiration with respect to PEP/LVEP during expiration exceeds a specified threshold, then a restrictive or obstructive respiratory condition may be deemed detected at 650.

The detected restrictive or obstructive respiratory condition, as determined at 650, may be provided to a user or a process at 550. If none of the HS components satisfies the condition as specified at 640, or a specified logical combination of the HS components fails to satisfy the specified condition at 640, then no restrictive or obstructive respiratory condition is deemed detected at 660. The process of detecting the restrictive or obstructive respiratory conditions may proceed to 610 to continue sensing the respiration and heart sounds signals.

The above detailed description includes references to the accompanying drawings, which form a part of the detailed description. The drawings show, by way of illustration, specific embodiments in which the disclosure may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the disclosure should be determined with reference to the appended claims, along with the full scope of equivalents to which such claims are entitled.

What is claimed is:

1. A system for managing a respiratory disease in a patient, comprising:
   a sensor circuit including sense amplifier circuits to sense one or more physiological signals including a respiration signal and at least one hemodynamic signal;
   a signal processor circuit configured to:
      detect from the respiration signal a respiratory phase within a respiratory cycle, the detected respiratory phase including a specific one of an inspiration phase or an expiration phase of the respiratory cycle; and
      generate from the sensed at least one hemodynamic signal, during the detected respiratory phase, one or more hemodynamic parameters correlative to at least one of a systolic blood pressure, a blood volume, or a cardiac dimension;
   a detector circuit coupled to the signal processor circuit and configured to detect a target restrictive or obstructive respiratory condition in response to the one or more hemodynamic parameters satisfying a specified condition during the detected respiratory phase; and
   an output circuit configured to provide the detected restrictive or obstructive respiratory condition to a user or a process.

2. The system of claim 1, comprising a therapy circuit configured to deliver a therapy to the patient in response to the detected restrictive or obstructive respiratory condition.

3. The system of claim 1, wherein the signal processor circuit is configured to detect the inspiration phase of the respiratory cycle, and
   wherein the detector circuit is configured to detect the target restrictive or obstructive respiratory condition in response to the one or more hemodynamic parameters indicating hemodynamic deterioration during at least a portion of the detected inspiration phase.

4. The system of claim 1, wherein the sensor circuit is coupled to a wearable or implantable accelerometer sensor or a microphone sensor to sense the respiration signal.

5. The system of claim 1, wherein:
   the sensor circuit is coupled to a heart sound sensor to sense the hemodynamic signal including a heart sound signal; and
   the signal processor circuit is to generate the one or more hemodynamic parameters including one or more of first (S1), second (S2), third (S3) and fourth (S4) heart sounds from the sensed heart sound signal during the detected respiratory phase of the respiration signal.

6. The system of claim 5, wherein the signal processor circuit is configured to detect the inspiration phase of the respiratory cycle and, separately, the expiration phase of the respiratory cycle, and
   wherein the detector circuit is configured to detect the restrictive or obstructive respiratory condition using one or more of:
   a S1 heart sound intensity during the detected inspiration phase;
   a S2 heart sound intensity during the detected inspiration phase;
   a S1 heart sound intensity during the detected inspiration phase relative to a S1 heart sound intensity during the detected expiration phase;
   a rate of change of the S1 heart sound intensity during the detected inspiration phase; or
   a rate of change of the S2 heart sound intensity during the detected inspiration phase.

7. The system of claim 5, wherein the signal processor circuit is configured to generate the one or more hemodynamic parameters including a relative intensity between one of the S1, S2, S3, or S4 heart sound and another of the S1, S2, S3, or S4 heart sound.

8. The system of claim 5, wherein the signal processor circuit is configured to generate the one or more hemodynamic parameters including a cardiac timing interval using the S1, S2, S3, or S4 heart sound.

9. The system of claim 1, wherein the signal processor circuit is configured to generate from the at least one hemodynamic signal the one or more hemodynamic parameters including:
   a heart rate;
   a cardiac or thoracic pressure metric;
   a left ventricular (LV) or right ventricular (RV) systolic volume, diastolic volume, or stroke volume metric;
   an ejection time;
   a cardiac output metric;
   a ratio of early to late ventricular filling velocities;
   a cardiac or thoracic impedance metric; or
   a photo plethysmography metric.

10. The system of claim 1, further comprising a physiological sensor configured to sense a signal indicative of respiratory sounds, wherein the detector circuit is configured to detect the restrictive or obstructive respiratory condition further using the respiratory sounds.

11. The system of claim 1, further comprising a classifier circuit configured to:
    trend the one or more hemodynamic parameters; and
    classify the detected restrictive or obstructive respiratory condition into one of two or more categories of restrictive or obstructive respiratory diseases using the trended one or more hemodynamic parameters,
    wherein the two or more categories of the restrictive or obstructive respiratory diseases include wheezing, asthma, bronchoconstriction, chronic obstructive pulmonary disease, bronchiectasis, acute bronchitis, pulmonary fibrosis, pneumoconiosis, acute respiratory distress syndrome, or sleep apnea.

12. The system of claim 11, further comprising one or more of:
    a physical activity detector to detect a physical activity intensity;
    a posture detector to detect a posture of the patient; or
    a sleep detector to detect a sleep or awake state,
    wherein the classifier circuit is to classify the detected restrictive or obstructive respiratory condition further using one or more of the detected physical activity level, the patient posture, or the sleep or awake state.

13. A method for detecting a respiratory condition in a patient using a respiratory disease management system, the method comprising:
    sensing, via an implantable or wearable physiological sensor, one or more physiological signals including a respiration signal and at least one hemodynamic signal;
    detecting from the respiration signal a respiratory phase within a respiratory cycle, the detected respiratory phase including a specific one of an inspiration phase or an expiration phase of the respiratory cycle;
    generating one or more hemodynamic parameters using the sensed at least one hemodynamic signal during the detected respiratory phase, the one or more hemodynamic parameters correlative to at least one of a systolic blood pressure, a blood volume, or a cardiac dimension;

detecting a target restrictive or obstructive respiratory condition in response to the one or more hemodynamic parameters satisfying a specified condition during the detected respiratory phase; and providing the detected restrictive or obstructive respiratory condition to a user or a process.

14. The method of claim 13, further comprising generating a signal to trigger or adjust a therapy delivered to the patient.

15. The method of claim 13, wherein detecting the respiratory phase includes detecting the inspiration phase of the respiratory cycle, and wherein detecting the target restrictive or obstructive respiratory condition includes detecting a hemodynamic deterioration from the one or more hemodynamic parameters during at least a portion of the detected inspiration phase.

16. The method of claim 13, wherein the at least one hemodynamic signal includes a heart sound signal and the one or more hemodynamic parameters include one or more of a first (S1), second (S2), third (S3) and fourth (S4) heart sounds from the sensed heart sound signal.

17. The method of claim 16, wherein detecting the restrictive or obstructive respiratory condition includes determining an intensity, or a rate of change of intensity, of one or more of S1, S2, S3, or S4 heart sounds during the detected inspiration phase satisfying a specified condition.

18. The method of claim 16, wherein the one or more hemodynamic parameters include:

a relative intensity between one of the S1, S2, S3, or S4 heart sound and another of the S1, S2, S3, or S4 heart sound; or a cardiac timing interval using the S1, S2, S3, or S4 heart sound.

19. The method of claim 13, further comprising sensing a signal indicative of respiratory sounds, wherein detecting the restrictive or obstructive respiratory condition further includes using the respiratory sounds.

20. The method of claim 13, further comprising:

trending the one or more hemodynamic parameters; and classifying the detected restrictive or obstructive respiratory condition into one of two or more categories of restrictive or obstructive respiratory diseases using the trended one or more hemodynamic parameters, wherein the two or more categories of the restrictive or obstructive respiratory diseases include wheezing, asthma, bronchoconstriction, chronic obstructive pulmonary disease, bronchiectasis, acute bronchitis, pulmonary fibrosis, pneumoconiosis, acute respiratory distress syndrome, or sleep apnea.

* * * * *